(12) United States Patent
Wang et al.

(10) Patent No.: US 12,116,332 B2
(45) Date of Patent: Oct. 15, 2024

(54) HIGH PURITY HFO-E-1,3,3,3-TETRAFLUOROPROPENE (trans-HFO-1234ze) AND METHODS FOR PRODUCING SAME

(71) Applicant: Honeywell International Inc., Charlotte, NC (US)

(72) Inventors: Haiyou Wang, Amherst, NY (US); Gustavo Cerri, Parsippany, NJ (US); Mitchel Cohn, Tonawanda, NY (US); Selma Bektesevic, Williamsville, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 18/071,610

(22) Filed: Nov. 29, 2022

(65) Prior Publication Data
US 2023/0174442 A1  Jun. 8, 2023

Related U.S. Application Data

(60) Provisional application No. 63/285,541, filed on Dec. 3, 2021.

(51) Int. Cl.
*C07C 17/25* (2006.01)
*C07C 17/358* (2006.01)
*C07C 17/38* (2006.01)
*C07C 17/383* (2006.01)
*C07C 17/395* (2006.01)
*C07C 21/18* (2006.01)

(52) U.S. Cl.
CPC .............. *C07C 21/18* (2013.01); *C07C 17/25* (2013.01); *C07C 17/358* (2013.01); *C07C 17/38* (2013.01); *C07C 17/383* (2013.01); *C07C 17/395* (2013.01)

(58) Field of Classification Search
CPC ..................................................... C07C 17/25
See application file for complete search history.

(56) References Cited

U.S. PATENT DOCUMENTS

| 5,710,352 A | 1/1998 | Tung |
| 5,895,825 A | 4/1999 | Elsheikh et al. |
| 6,124,510 A | 9/2000 | Elsheikh et al. |
| 6,472,573 B1 | 10/2002 | Yamamoto et al. |

(Continued)

FOREIGN PATENT DOCUMENTS

| CN | 106946647 A | 7/2017 |
| EP | 0939071 B1 | 7/2003 |
| WO | 2021217136 A1 | 10/2021 |

OTHER PUBLICATIONS

International Search Report and Written Opinion issued in International Application PCT/US2022/080738, mailed Apr. 6, 2023, 16 pages.

*Primary Examiner* — Medhanit W Bahta
(74) *Attorney, Agent, or Firm* — Faegre Drinker Biddle & Reath LLP

(57) ABSTRACT

The present disclosure provides high purity E-1,3,3,3-tetrafluoropropene (HFO-1234ze). More specifically, the present disclosure provides E-1,3,3,3-tetrafluoropropene (HFO-234ze) in at least 99.99% purity, containing less than 3 ppm 1,1,3,3,3-pentafluoropropene (HFO-1225zc). The present disclosure further provides a method of making high purity E-1,3,3,3-tetrafluoropropene (HFO-1234ze).

17 Claims, 5 Drawing Sheets

(56) References Cited

U.S. PATENT DOCUMENTS

| | | |
|---|---|---|
| 7,312,367 B2 | 12/2007 | Tung et al. |
| 7,485,760 B2 | 2/2009 | Wang et al. |
| 9,174,897 B2 * | 11/2015 | Imura .................. C07C 17/389 |
| 9,255,046 B2 | 2/2016 | Cottrell et al. |
| 11,718,775 B2 | 8/2023 | Peng et al. |
| 2012/0059200 A1 * | 3/2012 | Pokrovski ............. C01B 7/0706 570/160 |
| 2013/0261353 A1 | 10/2013 | Pokrovski et al. |
| 2019/0127301 A1 | 5/2019 | Pigamo et al. |

* cited by examiner

HIGH PURITY HFO-E-1,3,3,3-TETRAFLUOROPROPENE (trans-HFO-1234ze) AND METHODS FOR PRODUCING SAME

CROSS-REFERENCE TO RELATED APPLICATION

This application claims priority to U.S. Provisional Application No. 63/285,541, filed Dec. 3, 2021, which is herein incorporated by reference in its entirety.

FIELD

The present disclosure is related to high purity HFO-E-1,3,3,3-tetrafluoropropene (trans-HFO-1234ze), and methods for producing same.

BACKGROUND

Chlorofluorocarbons (CFCs) like trichlorofluoromethane and dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids. In this regard, E-1,3,3,3-tetrafluoropropene (trans HFO-1234ze) is a compound that has the potential to be used as a zero Ozone Depletion Potential (ODP) and a low Global Warming Potential (GWP) refrigerant, blowing agent, aerosol propellant, solvent, etc, and also as a fluorinated monomer.

It is known in the art to produce HFO-1234ze (i.e., HydroFluoroOlefin-1234ze). For example, U.S. Pat. No. 5,710,352 teaches the fluorination of 1,1,1,3,3-pentachloropropane (HCC-240fa) to form HCFC-1233zd and a small amount of HFO-1234ze. U.S. Pat. No. 5,895,825 teaches the fluorination of HCFC-1233zd to form HFO-1234ze. U.S. Pat. No. 6,472,573 also teaches the fluorination of HCFC-1233zd to form HFO-1234ze. U.S. Pat. No. 7,485,760 teaches production of HFO-1234ze by dehydrofluorination of 1,1,1,3,3-pentafluoropropane (HFC-245fa). U.S. Pat. No. 6,124,510 teaches the formation of cis and trans isomers of HFO-1234ze by the dehydrofluorination of HFC-245fa in the presence of an oxygen-containing gas using either a strong base or a chromium-based catalyst. European patent EP 0939071 describes the formation of HFC-245fa via the fluorination of HCC-240fa through intermediate reaction product which is an azeotropic mixture of HCFC-1233zd and HFO-1234ze.

SUMMARY

The present disclosure provides high purity and ultra-pureHFO-E-1,3,3,3-tetrafluoropropene (trans-HFO-1234ze), wherein the HFO-E-1,3,3,3-tetrafluoropropene (trans-HFO-1234ze) is at least 99.99% pure and includes 5 ppm or less 1,1,3,3,3-pentafluoropropene (HFO-1225zc).

The present disclosure also provides a method of making HFO-E-1,3,3,3-tetrafluoropropene (trans-HFO-1234ze), the method including (a) purifying a stream 1,1,1,3,3-pentafluoropropane (HFC-245fa); (b) dehydrofluorinating the purified stream of 1,1,1,3,3-pentafluoropropane (HFC-245fa) to thereby produce a result comprising HFO-Z-1,3,3,3-tetrafluoropropene (cis-HFO-1234ze), HFO-E-1,3,3,3-tetrafluoropropene (trans-HFO-1234ze), and hydrogen fluoride; (c) optionally recovering hydrogen fluoride from the result of step (b); (d) isomerizing at least a portion of the HFO-Z-1,3,3,3-tetrafluoropropene (cis-HFO-1234ze) into HFO-E-1,3,3,3-tetrafluoropropene (trans-HFO-1234ze); (e) passing the HFO-E-1,3,3,3-tetrafluoropropene (trans-HFO-1234ze) through at least one column; and (f) recovering purified HFO-E-1,3,3,3-tetrafluoropropene (trans-HFO-1234ze).

DETAILED DESCRIPTION

The present disclosure provides a high purity and ultra-pure HFO-E-1,3,3,3-tetrafluoropropene (trans-HFO-1234ze). More specifically, the present disclosure provides HFO-E-1,3,3,3-tetrafluoropropene (trans-HFO-1234ze) having at least 99.99% purity.

It is desirable to produce high purity HFO-E-1,3,3,3-tetrafluoropropene (trans-HFO-1234ze), for example, in medical application such as Metered Dose Inhalers (MDIs). However, in the event that HFO-E-1,3,3,3-tetrafluoropropene (trans-HFO-1234ze) is found to include small amounts of impurities, such as 1,1,3,3,3-pentafluoropropene (HFO-1225zc), 3,3,3-trifluoropropene (HFO-1243zf), 2,3,3,3-tetrafluoropropene (HFO-1234yf), and 1,1,1,2,2-pentafluoropropane (HFC-245cb), among others, for example. Such impurities, if present, may be mitigated using the methods provided herein.

However, methods such as distillation may prove challenging due to similarities in boiling points between the desired E-1,3,3,3-tetrafluoropropene (HFO-1234ze) and one or more of the impurities mentioned above. Furthermore, the small amounts in which the impurities may be present may make their removal difficult and resulting in loss of the desired product. Thus, it is desirable to prevent the formation of impurities in the production of E-1,3,3,3-tetrafluoropropene (HFO-1234ze), thereby lessening or removing the need for difficult purification steps. The present disclosure provides a method of reducing amounts of impurities found in HFO-E-1,3,3,3-tetrafluoropropene (trans-HFO-1234ze), in part, by providing purified stream of the reaction starting material.

The present disclosure provides a process for the production of high purity HFO-E-1,3,3,3-tetrafluoropropene (trans-HFO-1234ze) which comprises:
(a) purifying a stream 1,1,1,3,3-pentafluoropropane (HFC-245fa);
(b) dehydrofluorinating the purified stream of 1,1,1,3,3-pentafluoropropane (HFC-245fa) to thereby produce a result comprising HFO-Z-1,3,3,3-tetrafluoropropene (cis-HFO-1234ze), HFO-E-1,3,3,3-tetrafluoropropene (trans-HFO-1234ze) and hydrogen fluoride;
(c) optionally recovering hydrogen fluoride from the result of step (b);
(d) isomerizing at least a portion of the HFO-Z-1,3,3,3-tetrafluoropropene (cis-HFO-1234ze) into HFO-E-1,3,3,3-tetrafluoropropene (trans-HFO-1234ze);
(e) passing the E HFO-E-1,3,3,3-tetrafluoropropene (trans-HFO-1234ze) through at least one column; and
(f) recovering high purity HFO-E-1,3,3,3-tetrafluoropropene (trans-HFO-1234ze).

The process may be conducted as an integrated process or a batch process.

Figure 1:
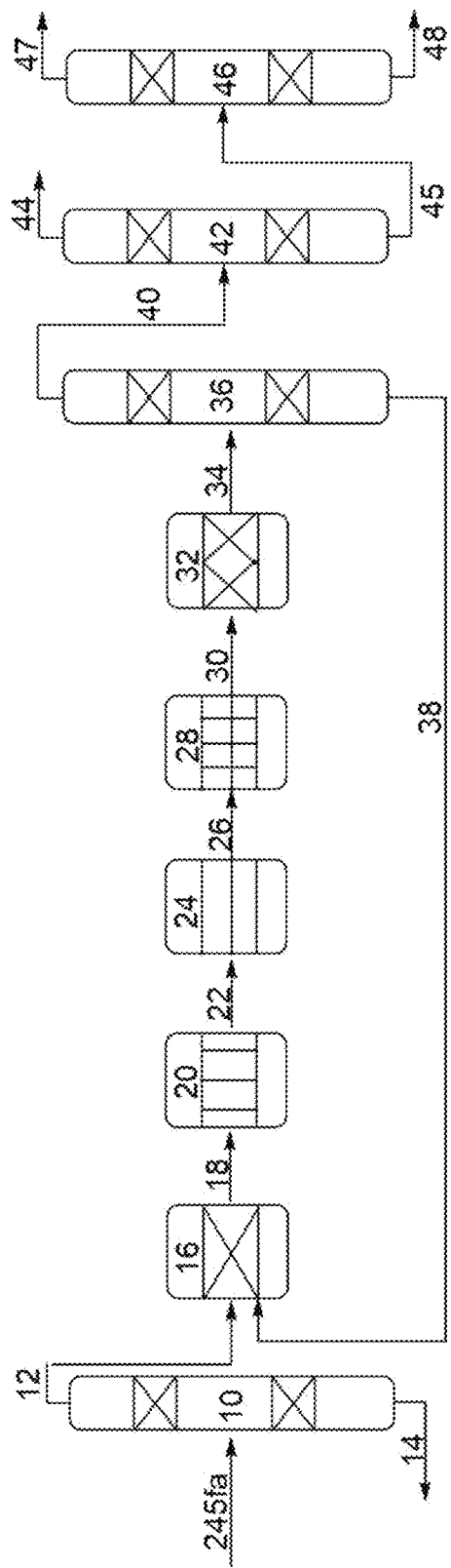
FIG. 1 shows a process diagram for the formation and purification of HFO-E-1,3,3,3-tetrafluoropropene (trans-HFO-1234ze).

An example of the process is shown in FIG. 1. As shown therein, a stream of 1,1,1,3,3-pentafluoropropane (HFC-245fa) may be passed through a distillation column 10 to remove high boiling impurities 14. The purified HFC-245fa 12 may then be passed to a reactor 16 to produce a product stream 18 comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa) and hydrogen fluoride (HF). The product stream 18 may then be passed to a water scrubber 20 to produce a stream 22 comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), water, and a lesser amount of HF. Stream 22 may then be passed to a caustic scrubber 24 to remove residual HF and provide a stream 26 comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), and water. Stream 26 may then be passed to a sulfuric acid drier 28 to remove residual water and produce a stream 30 comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), and residual acids such as HF. The stream 30 may then be passed to a mixed alumina/molecular sieve bed 32 to remove residual acids and moisture and produce a stream 34 comprising HFO-Z-1,3,3,3-tetrafluoropropene (cis-HFO-1234ze), HFO-E-1,3,3,3-tetrafluoropropene (trans-HFO-1234ze), and 1,1,1,3,3-pentafluoropropane (HFC-245fa). Stream 34 may then be passed to a distillation column 36 to provide a stream 38 comprising HFO-Z-1,3,3,3-tetrafluoropropene (cis-HFO-1234ze) and HFC-245fa. Stream 38 may be recycled back to reactor 16 for isomerization and further reaction. Stream 40 comprising low-boiling impurities and HFO-E-1,3,3,3-tetrafluoropropene (trans-HFO-1234ze) may then be passed to a second distillation column 42 to provide an overhead stream 44 comprising impurities which may be purged, and a stream 45 comprising HFO-E-1,3,3,3-tetrafluoropropene (trans-HFO-1234ze), which may be passed to a third distillation column 46. A stream 48 comprising high-boiling impurities may be purged, and an overhead stream 44 comprising purified HFO-E-1,3,3,3-tetrafluoropropene (trans-HFO-1234ze) may be passed on for storage.

The stream comprising HFO-E-1,3,3,3-tetrafluoropropene (trans-HFO-1234ze) may be passed through both 42, and 46; alternatively, the stream comprising HFO-E-1,3,3,3-tetrafluoropropene (trans-HFO-1234ze) may be through only column 42. As a further alternative, the stream comprising HFO-E-1,3,3,3-tetrafluoropropene (trans-HFO-1234ze) may be passed through columns 42, 46, and additional columns not shown in FIG. 1.

The purification of 1,1,1,3,3-pentafluoropropane (HFC-245fa) may be accomplished by passing the 1,1,1,3,3-pentafluoropropane (HFC-245fa) through one or more distillation columns to remove low-boiling and/or high-boiling impurities.

Without wishing to be bound by theory, it has been observed that impurities found in 1,1,1,3,3-pentafluoropropane (HFC-245fa), such as 1-chloro-1,1,3,3,3-pentafluoropropane (HFC-235fa) for example, may give rise to the formation of undesired impurities in the product HFO-E-1,3,3,3-tetrafluoropropene (trans-HFO-1234ze), such as 1,1,3,3,3-pentafluoropropene (HFC-1225zc), 3,3,3-trifluoropropene (HFO-1243zf), 2,3,3,3-tetrafluoropropene (HFO-1234yf), and 1,1,1,2,2-pentafluoropropane (HFC-245cb), among others, for example.

Among the impurities removed from 1,1,1,3,3-pentafluoropropane (HFC-245fa) may be 1-chloro-1,1,3,3,3-pentafluoropropane (HFC-235fa), 2-chloro-1,1,3,3,3-pentafluoropropane (HFC-235da), 1,1,1,3,3,3-hexafluoropropane (HFC-236fa), and 1,1,2,3,3,3-hexafluoropropane (HFC-236ea), for example.

A distillation column may be used to remove low boiling impurities from 1,1,1,3,3-pentafluoropropane (HFC-245fa), including 1,1,1,3,3,3-hexafluoropropane (HFC-236fa). The distillation column may operate in continuous mode at a pressure about 0 psig or greater, about 10 psig or greater, about 20 psig or greater, about 50 psig or greater, about 70 psig or less, about 100 psig or less, about 120 psig or less, about 150 psig or less, about 170 psig or less, about 200 psig or less, or any value or range encompassed by these endpoints.

The distillation column may use a reflux/feed ratio of about 0.5 or higher. The distillate rate may be selected to effectively remove the 1,1,1,3,3,3-hexafluoropropane (HFC-236fa) in the feed so that it is reduced in the bottom 1,1,1,3,3-pentafluoropropane (HFC-245fa) product from the column to the desired level.

A distillation column may be used to remove high boiling impurities from 1,1,1,3,3-pentafluoropropane (HFC-245fa), including 1-chloro-1,1,3,3,3-pentafluoropropane (HFC-235fa) and 2-chloro-1,1,3,3,3-pentafluoropropane (HFC-235da). The distillation column may be operated at a pressure of about 30 psig or greater, about 50 psig or greater, about 70 psig or greater, about 100 psig or less, about 120 psig or less, about 150 psig or less, about 170 psig or less, about 200 psig or less, or any value or range encompassed by these endpoints.

The distillation column may be operated with a reflux/feed ratio of about 2 or higher. The bottoms product rate may be chosen to effectively remove the 1-chloro-1,1,3,3,3-pentafluoropropane (HFC-235fa) and 2-chloro-1,1,3,3,3-pentafluoropropane (HFC-235da) in the feed so they are reduced in the distillate 1,1,1,3,3-pentafluoropropane (HFC-245fa) product from the column to the desired level.

The purified 1,1,1,3,3-pentafluoropropane (HFC-245fa) may include 1-chloro-1,1,3,3,3-pentafluoropropane (HFC-235fa) in an amount of about 250 ppm or less, about 200 ppm or less, about 150 ppm or less, about 100 ppm or less, about 50 ppm or less, about 40 ppm or more, about 30 ppm or more, about 20 ppm or more, about 10 ppm or more, about 5 ppm or more, about 1 ppm or more, or any value or range encompassed by any two of the foregoing values as endpoints.

The purified 1,1,1,3,3-pentafluoropropane (HFC-245fa) may include 2-chloro-1,1,3,3,3-pentafluoropropane (HFC-235da) in an amount of about 250 ppm or less, about 200 ppm or less, about 150 ppm or less, about 100 ppm or less, about 50 ppm or less, about 40 ppm or more, about 30 ppm or more, about 20 ppm or more, about 10 ppm or more, about 5 ppm or more, about 1 ppm or more, or any value or range encompassed by any two of the foregoing values as endpoints.

The purified 1,1,1,3,3-pentafluoropropane (HFC-245fa) may include 1,1,1,3,3,3-hexafluoropropane (HFC-236fa) in an amount of about 250 ppm or less, about 200 ppm or less, about 150 ppm or less, about 100 ppm or less, about 50 ppm or less, about 40 ppm or more, about 30 ppm or more, about 20 ppm or more, about 10 ppm or more, about 5 ppm or more, about 1 ppm or more, or any value or range encompassed by any two of the foregoing values as endpoints.

The purified 1,1,1,3,3-pentafluoropropane (HFC-245fa) may include 1,1,2,3,3,3-hexafluoropropane (HFC-236ea) in an amount of about 250 ppm or less, about 200 ppm or less, about 150 ppm or less, about 100 ppm or less, about 50 ppm or less, about 40 ppm or more, about 30 ppm or more, about 20 ppm or more, about 10 ppm or more, about 5 ppm or more, about 1 ppm or more, or any value or range encompassed by any two of the foregoing values as endpoints.

The second step of the process involves the catalytic conversion of HFC-245fa by dehydrofluorinating HFC-245fa to produce a result comprising a combination of HFO-Z-1,3,3,3-tetrafluoropropene (cis-HFO-1234ze), HFO-E-1,3,3,3-tetrafluoropropene (trans-HFO-1234ze), and hydrogen fluoride. Dehydrofluorination reactions are well known in the art. Preferably dehydrofluorination of HFC-245fa is done in a vapor phase, and more preferably in a fixed-bed reactor in the vapor phase. The dehydrofluorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single pipe or multiple tubes packed with a dehydrofluorinating catalyst which may be one or more of fluorinated metal oxides in bulk form or supported, metal halides in bulk form or supported, and carbon supported transition metals, metal oxides and halides.

Suitable catalysts non-exclusively include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C.

Useful reaction temperatures may range from about 100° C. to about 600° C. Preferred temperatures may range from about 150° C. to about 450° C., and more preferred temperatures may range from about 200° C. to about 350° C.

The reaction may be conducted at atmospheric pressure, super-atmospheric pressure or under vacuum. The vacuum pressure can be from about 5 torr to about 760 torr.

Contact time of the HFC-245fa with the catalyst may range from about 0.5 seconds to about 120 seconds, however, longer or shorter times can be used.

In an embodiment, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days. This is followed by either HF treatment at temperatures of from about 25° C. to about 400° C., preferably from about 200° C. to about 350° C. for fluorinated metal oxide catalysts and metal fluoride ones or $H_2$ treatment at temperatures of from about 100° C. to about 400° C., preferably from about 200° C. to about 350° C. for carbon supported transition metal catalysts.

In an alternative embodiment of the invention, dehydrofluorination of HFC-245fa can also be accomplished by reacting it with a strong caustic solution that includes, but is not limited to KOH, NaOH, $Ca(OH)_2$ and CaO at an elevated temperature. In this case, the caustic strength of the caustic solution is of from about 2 wt. % to about 100 wt. %, more preferably from about 5 wt. % to about 90 wt. % and most preferably from about 10 wt. % to about 80 wt. %.

The reaction may be conducted at a temperature of from about 20° C. to about 100° C., more preferably from about 30° C. to about 90° C. and most preferably from about 40° C. to about 80° C.

As above, the reaction may be conducted at atmospheric pressure, super-atmospheric pressure or under vacuum. The vacuum pressure can be from about 5 torr to about 760 torr. In addition, a solvent may optionally be used to help dissolve the organic compounds in the caustic solution. This optional step may be conducted using solvents that are well known in the art for said purpose.

Once the stream comprising HFO-E-1,3,3,3-tetrafluoropropene (trans-HFO-1234ze) has passed through the water scrubber, the caustic scrubber, and the sulfuric acid drier, the stream may be further purified by distillation. Specifically, one or multiple distillation columns may be run as a batch or continuous process to reduce the levels of impurities in HFO-E-1,3,3,3-tetrafluoropropene (trans-HFO-1234ze).

The purification process may result in a product stream comprising high purity HFO-E-1,3,3,3-tetrafluoropropene (trans-HFO-1234ze).

Specifically, the high purity HFO-E-1,3,3,3-tetrafluoropropene (trans-HFO-1234ze) may have a purity of about 99.99% or greater, about 99.999% or greater, or about 99.9995% or greater.

The high purity HFO-E-1,3,3,3-tetrafluoropropene (trans-HFO-1234ze) may include trace amounts of impurities. For example, the high purity HFO-E-1,3,3,3-tetrafluoropropene (trans-HFO-1234ze) may include 1,1,3,3,3-pentafluoropropene (HFO-1225zc) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS) where the GC/MS instrument was calibrated with a standard sample with known amounts of the impurities.

The high purity HFO-E-1,3,3,3-tetrafluoropropene (trans-HFO-1234ze) may include HFO-Z-1,3,3,3-tetrafluoropropene (cis-HFO-1234ze) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 3,3,3-trifluoropropene (HFO- 1243zf) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 3,3,3-trifluoropropyne in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 2,3,3,3-tetrafluoropropene (HFO-1234yf) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 1,1,3,3-tetrafluoropropene (HFO-1234zc) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include E-1-chloro-3,3,3-trifluoropropene (HFO-1233zdE) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 1,1,1,3,3-pentafluoropropene (HFC-245fa) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 1,1,1,2,2-pentafluoropropane (HFC-245cb) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include Z-1,2,3,3,3-pentafluoropropane (HFO-1225ye(Z)) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include E-1,2,3,3,3-pentafluoropropane (HFO-1225ye(E)) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 1,2-dichlorotetrafluoroethane (CFC-114) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 2-chloro-1,1,1-2-tetrafluoroethane (HCFC-124) in an amount of about 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include 1,1-difluoroethane (HFC-152a) in an amount of 5 ppm or less, about 4 ppm or less, about 3 ppm or less, about 2 ppm or less, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include water in an amount of about 20 ppm or less, about 15 ppm or less, about 10 ppm or less, about 5 ppm or more, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include hydrochloric acid (HCl) in an amount of about 1 ppm or less, about 0.5 ppm or less, about 0.1 ppm or more, about 0.01 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include non-volatile residue in an amount of about 50 ppm or less, about 40 ppm or less, about 30 ppm or less, about 20 ppm or less, about 15 ppm or less, about 10 ppm or less, about 5 ppm or more, about 1 ppm or more, about 0.5 ppm or more, about 0.1 ppm or more, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include a total amount of unsaturated impurities in an amount of about 10 ppm or less, about 5 ppm or less, about 1 ppm or more, about 0.5 ppm or less, about 0.1 ppm or less, or any value or range encompassed by any two of the foregoing values as endpoints, as determined by gas chromatography/mass spectrometry (GC/MS).

The high purity HFO-E-1,3,3,3-tetrafluoropropene (trans-HFO-1234ze) may include a total amount of saturated impurities in an amount of about 10 ppm or less, about 5 ppm or less, about 1 ppm or more, about 0.5 ppm or less, about 0.1 ppm or more, or any value or range encompassed by any two of the foregoing values as endpoints, as determined by gas chromatography/mass spectrometry (GC/MS).

EXAMPLES

Example 1

Production of High Purity
HFO-E-1,3,3,3-tetrafluoropropene
(Trans-HFO-1234ze)

A stream of 1,1,1,3,3-pentafluoropropane (HFC-245fa) is passed through a distillation column, then to a reactor to produce a product stream comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa) and hydrogen fluoride (HF). The product stream is then passed to a water scrubber to produce a stream comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), water, and a lesser amount of HF. This stream is then passed through a caustic scrubber to remove residual HF and provide a stream comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), and water. This stream is then passed to a sulfuric acid drier to remove residual water and produce a stream comprising HFO-Z-1,3,3,3-tetrafluoropropene (cis-HFO-1234ze), HFO-E-1,3,3,3-tetrafluoropropene (trans-HFO-1234ze), 1,1,1,3,3-pentafluoropropane (HFC-245fa), and residual acids such as HF. The stream is then passed to a mixed alumina/molecular sieve bed to remove residual acids and water, producing a stream comprising HFO-Z-1,3,3,3-tetrafluoropropene (cis-HFO-1234ze), HFO-E-1,3,3,3-tetrafluoropropene (trans-HFO-1234ze), and 1,1,1,3,3-pentafluoropropane (HFC-245fa). The stream is then passed to a distillation column to provide a bottoms product comprising HFO-Z-1,3,3,3-tetrafluoropropene (cis-HFO-1234ze) and HFC-245fa and an overhead product comprising low-boiling impurities and HFO-E-1,3,3,3-tetrafluoropropene (trans-HFO-1234ze), which is then be passed to a second distillation column to provide a purified product stream comprising purified HFO-E-1,3,3,3-tetrafluoropropene (trans-HFO-1234ze).

The purified HFO-E-1,3,3,3-tetrafluoropropene (trans-HFO-1234ze) has a purity of greater than 99.99% and includes small amounts of impurities in the amounts shown in Table 1 below.

TABLE 1

| Compound | Amount |
|---|---|
| HFO-1225zc; 1.1.1.3.3-pentafluoropropene | ≤5 ppm w/w |
| HFO-1243zf; 3,3,3-Trifluoropropene | ≤5 ppm w/w |
| 3,3,3-Trifluoropropyne | ≤5 ppm w/w |
| HFO-1234yf; 2,3,3,3-Tetrafluoroprop-1-ene | ≤5 ppm w/w |
| HFC-245cb; 1,1,1,2,2-pentafluoropropane | ≤5 ppm w/w |
| HFO-1234zc; 1,1,3,3-tetrafluoroprop-1-ene | ≤5 ppm w/w |
| Cis-HFO-1234ze; Z-1,3,3,3-tetrafluoroprop-1-ene | ≤5 ppm w/w |
| Cis-HCFO-1233zd; Z-1-chloro-3,3,3-trifluoroprop-1-ene | ≤5 ppm w/w |
| CFC-114; 1,2-dichlorotetrafluoroethane | ≤5 ppm w/w |
| HFC-245fa; 1,1,1,3,3-pentafluoropropane | ≤5 ppm w/w |

Example 2

Dehydrofluorination of HFC-245fa With and Without HCFC-235Fa in Feed Stream

To test whether the presence of impurities, such as HCFC-235fa, in the HFC-245fa feed stream leads to the formation of HFO-1225zc during dehydrofluorination, two separate feed streams were prepared. One stream comprised HFC-245fa without HCFC-235fa, and the second comprised HFC-245fa with added HCFC-235fa.

Figure 2:
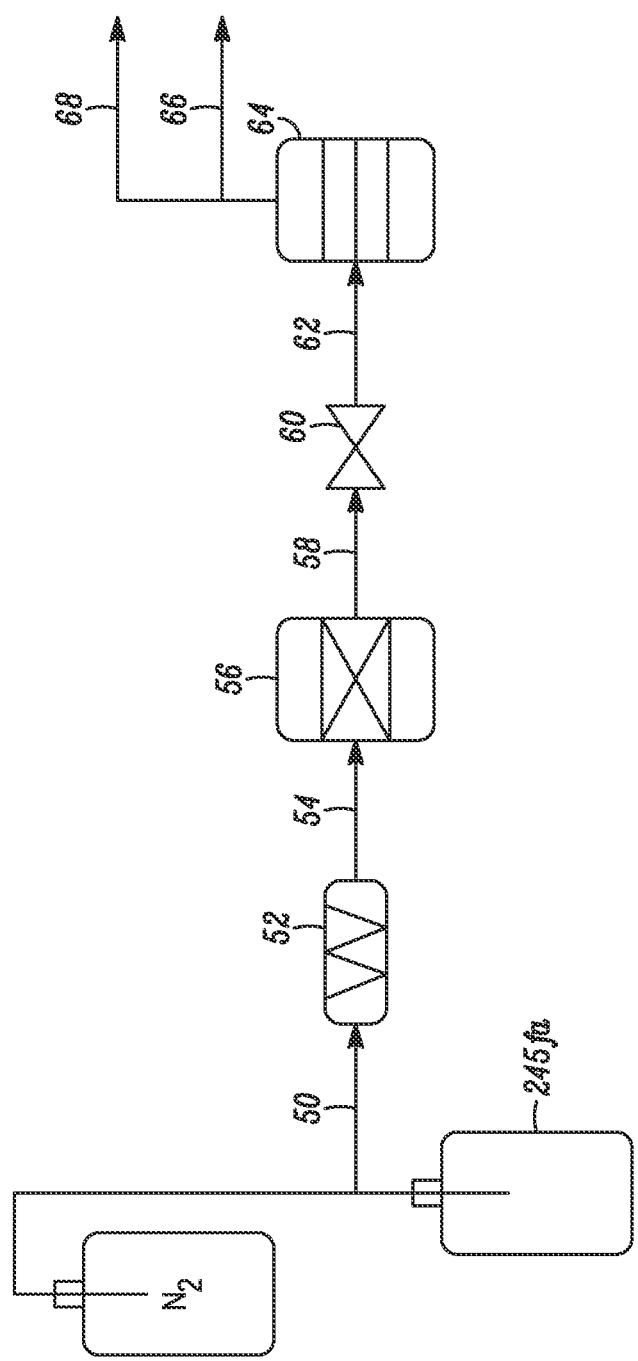
FIG. 2 shows a laboratory-scale experimental set-up for the dehydrofluorination of 1,1,1,3,3-pentafluoropropane (HFC-245fa), as described Example 1.

As shown in FIG. 2, the reaction system consists of feed delivery system 50, feed preheater (vaporizer) 52, reactor 56, pressure control system 60, caustic solution carboy 64, and sampling ports 66 and 68. One part of the feed system 50 is nitrogen. $N_2$ is used during heating and cooling the reactor. The other part of the feed system 50 is organic feed (245fa). The feed system is followed by vaporizer 52 and the reactor 56. Reactor pressure is controlled by RCV. After RCV, reactor effluent is passed through KOH solution carboy 64 to neutralize any acid formed during reaction. A 10% KOH solution was used.

Reactions were run in the single pass unit under conditions scaled down from those used in commercial plant. A ¾" Inconel 600 tube was utilized as the reactor. The amount of catalyst (chromia catalyst) charged was roughly 50 ml (about 10 inches of catalyst bed height). The reactor was heated to 300° C. under a nitrogen atmosphere, and the reaction was conducted at a pressure of 8 psig, using a 20 grams/hour feed rate.

Once the reactor reached the desired temperature, the feed was started. Reactor effluent samples were taken from the sampling port located on the KOH scrubber exit line after steady state was established and were analyzed to determine the amount of the HFO-1225zc impurity present.

Table 2 shows the analysis results of feed samples and reactor effluent samples taken during the HFC-245fa dehydrofluorination reaction at 300° C. As shown below, for reaction carried out at 300° C. using the HCFC-235fa-free HFC-245fa feed, no HFO-1225zc was detected in reactor effluent sample. Conversely, when the HFC-245fa feed including HCFC-235fa was used under the same reaction conditions, HFO-1225zc was detected.

TABLE 2

| | 235fa and 1225zc in feed | | 1234zeE and 1225zc in reactor effluent | |
|---|---|---|---|---|
| Feed | 235fa, ppm | 1225zc, ppm | 1234zeE, GC area % | 1225zc, ppm |
| 235fa-free 245fa feed | 0 | 0 | 40.15 | 0 |
| 245fa feed including 235-fa | 303 | 0 | 41.26 | 2.7 |

Table 3 shows the effect of reaction temperature on HFO-1225zc formation. As described above, the reaction was run using 50 mL of chromia catalyst at a pressure of 8 psig, with a feed rate of 20 grams/hour. As shown below, when the HFC-245fa feed stream included HCFC-235fa, the amount of HFO-1225zc increased from 2.7 ppm to 6.6 ppm as the reaction temperature was increased from 300° C. to 316° C. These results indicate the presence of HCFC-235fa in the HFC-245fa feed may lead to the formation of HFO-1225zc during the reaction and ultimately, for its presence in HFO-1234zeE product.

TABLE 3

| Feed | 235fa and 1225zc in feed | | 1234zeE and 1225zc in reactor effluent | |
|---|---|---|---|---|
| | 235fa, ppm | 1225zc, ppm | Reaction temp., °C. | 1234zeE, GC area % | 1225zc, ppm |
| 245fa feed including 235fa | 303 | 0 | 300 316 | 41.26 48.67 | 2.7 6.6 |

Example 3

Dehydrofluorination of HFC-245fa With and Without 1-chloro-1,1,3,3,3-pentafluoropropane (HFC-235fa), 2-chloro-1,1,3,3,3-pentafluoropropane (HFC-235da), 1,1,1,3,3,3-hexafluoropropane (HFC-236fa), and 1,1,2,3,3,3-hexafluoropropane (HFC-236ea) in Feed Stream To test whether the presence of impurities, such as 1-chloro-1,1,3,3,3-pentafluoropropane (HFC-235fa), 2-chloro-1,1,3,3,3-pentafluoropropane (HFC-235da), 1,1,1,3,3,3-hexafluoropropane (HFC-236fa), and 1,1,2,3,3,3-hexafluoropropane (HFC-236ea), in the HFC-245fa feed stream leads to the formation of HFO-1225zc during dehydrofluorination, five separate feed streams are prepared as shown in Table 4 below.

TABLE 4

| Feed stream # | Component 1 | Component 2 |
|---|---|---|
| 1 | HFC-245fa | — |
| 2 | HFC-245fa | HFC-235fa |
| 3 | HFC-245fa | HFC-235da |
| 4 | HFC-245fa | HFC-236fa |
| 5 | HFC-245fa | HFC-236ea |

The experiments are conducted in the same manner as described above in Example 2. Similar to the results observed in Example 2, HFO-1225zc is detected at elevated levels in the reactor effluents of runs 2-5 as comparted with run 1.

Example 4

Purification of HFC-245fa

A crude product stream comprising 98.0 wt. % HFC-245fa, 1.47 wt. % HCFC-235fa, 0.28 wt. % HFC-236fa and others is purified by distillation to reduce the amount of HFC-236fa and HCFC-235fa in the HFC-245fa product. The crude product stream is passed to a first distillation column to produce an overhead stream comprising HFC-236fa. The first bottom stream is fed to a second distillation column to produce a second bottoms stream comprising HCFC-235fa. The liquid distillate recovered from the second column comprises HFC-245fa with reduced amounts HFC-236fa and HCFC-235fa, which is used as the feed stream to synthesize HFO-1234ze.

The first column operates at 25 psig at a reflux ratio of about 450 and the second column operates at 35 psig at a reflux ratio of 3.4. The components of the streams described above are shown below in Table 5.

TABLE 5

| Stream | Column 1 feed | Column 1 overhead | Column 1 bottom | Column 2 distillate | Column 2 bottom |
|---|---|---|---|---|---|
| Wt. % 245fa | 98.0 | 53.8 | 98.3 | 99.95 | 21.6 |
| Wt. % 236fa | 0.28 | 44.8 | 0 | 0 | 0 |
| Wt. % 235fa | 1.47 | 0 | 1.48 | 0.02 | 68.4 |
| Others | Balance | Balance | Balance | Balance | Balance |

Example 5

Purification of HFO-1234ze

Figure 3:
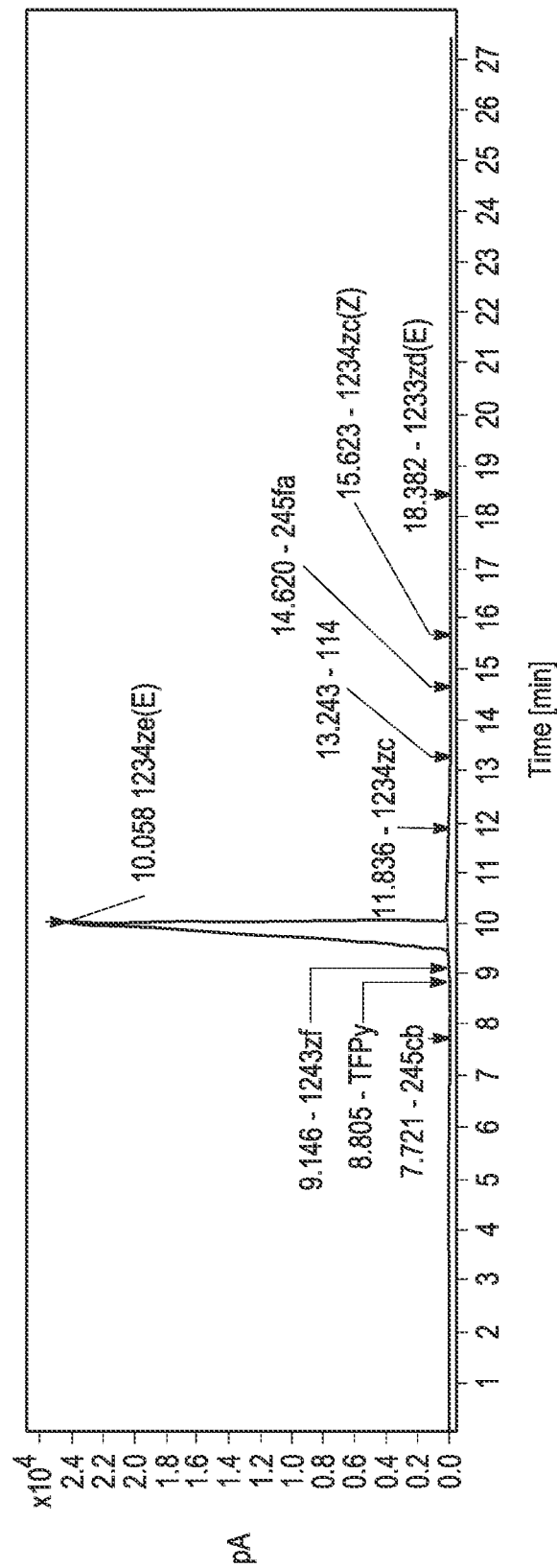
FIG. 3 shows a GC trace from monitoring the purification of HFO-E-1,3,3,3-tetrafluoropropene (trans-HFO-1234ze), as described in Example 5.

A batch distillation employing a single column with a reboiler and a single total condenser was performed at 50 psig, using a stainless steel column containing roughly 30-120 theoretical plates for separation. The crude HFO-1234zeE was loaded into the reboiler containing <99.98% HFO-1234zeE. The reboiler was then heated to an initial temperature of 22.0° C., with the column overhead at an initial temperature of 21.1° C. once reflux was achieved. Initial separation of the low boiling components was conducted with a reflux ratio was between 45:1 to 90:1. The distillate was collected in a tank for use as a byproduct. The lights removed included HFC-245cb, HFO-1234yf, HFO-1225zc, trifluoropropyne, and HFO-1243zf. The distillation was monitored by GC before, during, and after the distillation to measure the tracked impurities using a standard (e.g. 5 ppm) for each impurity as shown in Table 6 below. A GC trace is provided in FIG. 3.

TABLE 6

| Concentration (ppm) | | | | | | | | |
|---|---|---|---|---|---|---|---|---|
| Lights | | | | | Heavies | | | |
| 245cb + 1234yf + 1225zc | TFPy | 1243zf | 1234zc | 114 | 245fa | 1234ze(Z) | 1233zd(E) |
| 13.004 | 4.816 | 11.870 | 5.015 | 5.148 | 4.879 | 5.012 | 4.810 |

Figure 4:
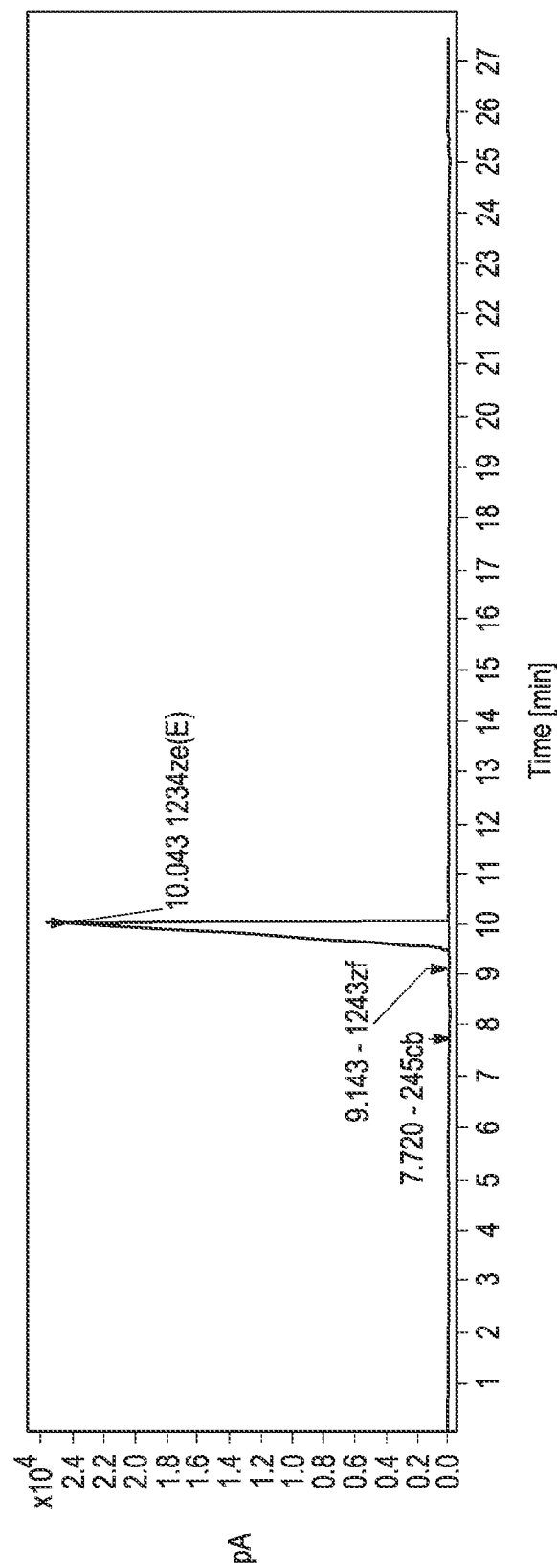
FIG. 4 shows a GC trace from monitoring the purification of HFO-E-1,3,3,3-tetrafluoropropene (trans-HFO-1234ze), as described in Example 5.

Once the analysis of the column reflux indicated that the key lights components (for example HFO-245cb and HFO-1225zc) levels were below a previously established point, such as 13 ppm, the distillate was collected in a separate product tank. The reflux ratio was then run at approximately 5:1 to 7:1 during the product take-off. Table 7 shows the results of GC analysis at the end of the lights cut and prior to the product cut, wherein ND signifies non-detectable. FIG. 4 shows the corresponding GC trace.

TABLE 7

| Lights | | | Heavies | | | | | |
|---|---|---|---|---|---|---|---|---|
| 245cb + 1234yf + 1225zc | TFPy | 1243zf | 1234zc | 114 | 245fa | 1234ze(Z) | 1233zd(E) | |
| 1.269 | | ND | 9.778 | ND | ND | ND | ND | ND |

During the product take-off, the heavy components (CFC-114, HFO-245fa, HFO-1234zeZ and HFO-1233zdE) were monitored by GC. Once the level of any of these heavies increased above a previously established threshold (for example 5 ppm), then the distillation was stopped. In this Example, the distillation was stopped once the amount of HFO-1234zeE collected in the product tank met the pre-established level of product for the batch.

Figure 5:
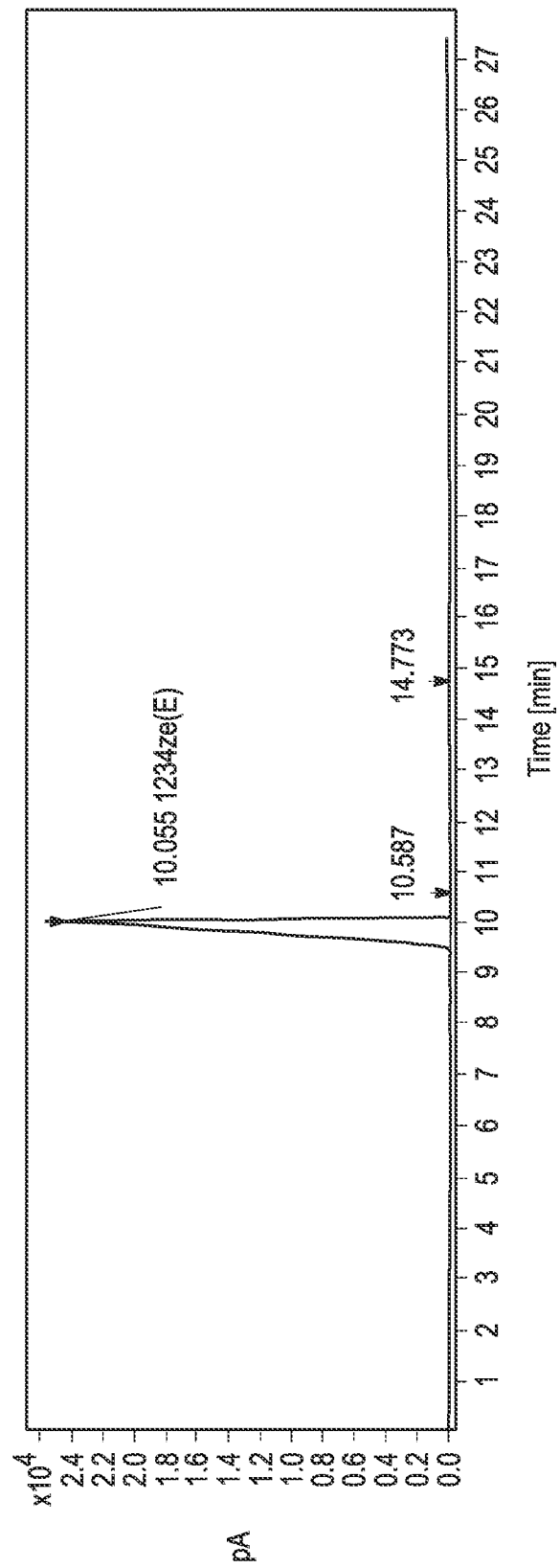
FIG. 5 shows a GC trace from monitoring the purification of HFO-E-1,3,3,3-tetrafluoropropene (trans-HFO-1234ze), as described in Example 5.

Analysis of the column reflux prior to terminating the distillation was performed. The final GC chromatogram is shown in FIG. 5, and the results are shown in Table 8. The levels of lights in this Example were low enough to be non-detectable (ND). The remaining liquid was collected with the heavy components from the reboiler as a byproduct.

TABLE 8

| Lights | | | Heavies | | | | | |
|---|---|---|---|---|---|---|---|---|
| 245cb + 1234yf + 1225zc | TFPy | 1243zf | 1234zc | 114 | 245fa | 1234ze(Z) | 1233zd(E) | |
| ND | ND | ND | ND | ND | ND | ND | ND | |

At the end of distillation, four samples were taken from product tank for analysis to determine the concentrations of HFO-1234zeE and organic impurities. The results showed i) HFO-1234zeE purity of the product was greater 99.9995 wt. %, ii) both the total unsaturated impurities and the total saturated impurities were less than 3 ppm (w/w), and iii) no individual organic impurity was more than 2 ppm (w/w).

ASPECTS

Aspect 1 is a composition comprising HFO-E-1,3,3,3-tetrafluoropropene (trans-HFO-1234ze), wherein the HFO-E-1,3,3,3-tetrafluoropropene (trans-HFO-1234ze) is at least 99.99% pure and includes 5 ppm or less 1,1,3,3,3-pentafluoropropene (HFO-1225zc).

Aspect 2 is the composition of Aspect 1, wherein the HFO-E-1,3,3,3-tetrafluoropropene (trans-HFO-1234ze) is at least 99.999% pure and includes 3 ppm or less 1,1,3,3,3-pentafluoropropene (HFO-1225zc).

Aspect 3 is the composition of either Aspect or Aspect 2, wherein the HFO-E-1,3,3,3-tetrafluoropropene (trans-HFO-1234ze) is at least 99.9995% pure and includes 3 ppm or less 1,1,3,3,3-pentafluoropropene (HFO-1225zc).

Aspect 4 is a method of making HFO-E-1,3,3,3-tetrafluoropropene (trans-HFO-1234ze), the method comprising:
(a) purifying a stream 1,1,1,3,3-pentafluoropropane (HFC-245fa);
(b) dehydrofluorinating the purified stream of 1,1,1,3,3-pentafluoropropane (HFC-245fa) to thereby produce a result comprising HFO-Z-1,3,3,3-tetrafluoropropene (cis-HFO-1234ze), HFO-E-1,3,3,3-tetrafluoropropene (trans-HFO-1234ze), and hydrogen fluoride;
(c) isomerizing at least a portion of the HFO-Z-1,3,3,3-tetrafluoropropene (cis-HFO-1234ze) into HFO-E-1,3,3,3-tetrafluoropropene (trans-HFO-1234ze);
(d) passing the HFO-E-1,3,3,3-tetrafluoropropene (trans-HFO-1234ze) through at least one column; and
(e) recovering purified HFO-E-1,3,3,3-tetrafluoropropene (trans-HFO-1234ze).

Aspect 5 is the method of Aspect 4, wherein step (a) further comprises passing a stream of a stream 1,1,1,3,3-pentafluoropropane (HFC-245fa) through one or more distillation columns to produce a purified stream of 1,1,1,3,3-pentafluoropropane (HFC-245fa).

Aspect 6 is the method of either Aspect 4 or Aspect 5, wherein the purified 1,1,1,3,3-pentafluoropropane (HFC-245fa) comprises 1-chloro-1,1,3,3,3-pentafluoropropane (HFC-235fa) in an amount of about 50 ppm or less.

Aspect 7 is the method of any of Aspects 4-6, wherein the purified 1,1,1,3,3-pentafluoropropane (HFC-245fa) comprises 2-chloro-1,1,3,3,3-pentafluoropropane (HFC-235da) in an amount of about 50 ppm or less.

Aspect 8 is the method of any of Aspects 4-7, wherein the purified 1,1,1,3,3-pentafluoropropane (HFC-245fa) comprises 1,1,1,3,3,3-hexafluoropropane (HFC-236fa) in an amount of about 50 ppm or less.

Aspect 9 is the method of any of Aspects 4-8, wherein the purified 1,1,1,3,3-pentafluoropropane (HFC-245fa) comprises 1,1,2,3,3,3-hexafluoropropane (HFC-236ea) in an amount of 50 ppm or less.

Aspect 10 is the method of any of Aspects 4-9, wherein the purified HFO-E-1,3,3,3-tetrafluoropropene (trans-HFO-1234ze) is at least 99.99% pure and includes 5 ppm or less 1,1,3,3,3-pentafluoropropene (HFO-1225zc).

Aspect 11 is the method of any of Aspects 4-10, wherein the purified HFO-E-1,3,3,3-tetrafluoropropene (trans-HFO-1234ze) is at least 99.999% pure and includes 3 ppm or less 1,1,3,3,3-pentafluoropropene (HFO-1225zc).

Aspect 12 is the method of any of Aspects 4-11, wherein the purified HFO-E-1,3,3,3-tetrafluoropropene (trans-HFO-1234ze) is at least 99.9995% pure and includes 3 ppm or less 1,1,3,3,3-pentafluoropropene (HFO-1225zc).

The invention claimed is:
1. A method of making HFO-E-1,3,3,3-tetrafluoropropene (trans-HFO-1234ze), the method comprising:
(a) purifying a stream of 1,1,1,3,3-pentafluoropropane (HFC-245fa);

(b) dehydrofluorinating the purified stream of 1,1,1,3,3-pentafluoropropane (HFC-245fa) to thereby produce a result comprising HFO-Z-1,3,3,3-tetrafluoropropene (cis-HFO-1234ze), HFO-E-1,3,3,3-tetrafluoropropene (trans-HFO-1234ze), and hydrogen fluoride;

(c) isomerizing at least a portion of the HFO-Z-1,3,3,3-tetrafluoropropene (cis-HFO-1234ze) into HFO-E-1,3,3,3-tetrafluoropropene (trans-HFO-1234ze);

(d) passing the HFO-E-1,3,3,3-tetrafluoropropene (trans-HFO-1234ze) through a water scrubber, a caustic scrubber and a sulfuric acid drier;

(e) passing the HFO-E-1,3,3,3-tetrafluoropropene (trans-HFO-1234ze) through at least one distillation column; and (f) recovering purified HFO-E-1,3,3,3-tetrafluoropropene (trans-HFO-1234ze) of at least 99.99% purity and including 5 ppm or less 1,1,3,3,3-pentafluoropropene (HFO-1225zc).

2. The method of claim 1, wherein step (a) further comprises passing a stream of a stream 1,1,1,3,3-pentafluoropropane (HFC-245fa) through one or more distillation columns to produce a purified stream of 1,1,1,3,3-pentafluoropropane (HFC-245fa).

3. The method of claim 1, wherein the purified 1,1,1,3,3-pentafluoropropane (HFC-245fa) comprises 1-chloro-1,1,3,3,3-pentafluoropropane (HFC-235fa) in an amount of about 50 ppm or less.

4. The method of claim 1, wherein the purified 1,1,1,3,3-pentafluoropropane (HFC-245fa) comprises 2-chloro-1,1,3,3,3-pentafluoropropane (HFC-235da) in an amount of about 50 ppm or less.

5. The method of claim 1, wherein the purified 1,1,1,3,3-pentafluoropropane (HFC-245fa) comprises 1,1,1,3,3,3-hexafluoropropane (HFC-236fa) in an amount of about 50 ppm or less.

6. The method of claim 1, wherein the purified 1,1,1,3,3-pentafluoropropane (HFC-245fa) comprises 1,1,2,3,3,3-hexafluoropropane (HFC-236ea) in an amount of 50 ppm or less.

7. The method of claim 1, wherein the purified HFO-E-1,3,3,3-tetrafluoropropene (trans-HFO-1234ze) is at least 99.999% pure and includes 3 ppm or less 1,1,3,3,3-pentafluoropropene (HFO-1225zc).

8. The method of claim 1, wherein the purified HFO-E-1,3,3,3-tetrafluoropropene (trans-HFO-1234ze) is at least 99.9995% pure and includes 3 ppm or less 1,1,3,3,3-pentafluoropropene (HFO-1225zc).

9. A method of making HFO-E-1,3,3,3-tetrafluoropropene (trans-HFO-1234ze), the method comprising:

(a) purifying a stream of 1,1,1,3,3-pentafluoropropane (HFC-245fa) by passing through one or more distillation columns to produce a purified stream of 1,1,1,3,3-pentafluoropropane (HFC-245fa) having a content of at least one of 1-chloro-1,1,3,3,3-pentafluoropropane (HFC-235fa), 2-chloro-1,1,3,3,3-pentafluoropropane (HFC-235da), 1,1,1,3,3,3-hexafluoropropane (HFC-236fa), and 1,1,2,3,3,3-hexafluoropropane (HFC-236ea) of about 50 ppm or less;

(b) dehydrofluorinating the purified stream of 1,1,1,3,3-pentafluoropropane (HFC-245fa) to thereby produce a result comprising HFO-Z-1,3,3,3-tetrafluoropropene (cis-HFO-1234ze), HFO-E-1,3,3,3-tetrafluoropropene (trans-HFO-1234ze), and hydrogen fluoride;

(c) isomerizing at least a portion of the HFO-Z-1,3,3,3-tetrafluoropropene (cis-HFO-1234ze) into HFO-E-1,3,3,3-tetrafluoropropene (trans-HFO-1234ze);

(d) passing the HFO-E-1,3,3,3-tetrafluoropropene (trans-HFO-1234ze) through at least one distillation column; and (e) recovering purified HFO-E-1,3,3,3-tetrafluoropropene (trans-HFO-1234ze) including 5 ppm or less 1,1,3,3,3-pentafluoropropene (HFO-1225zc).

10. The method of claim 9, wherein the purified 1,1,1,3,3-pentafluoropropane (HFC-245fa) comprises 1-chloro-1,1,3,3,3-pentafluoropropane (HFC-235fa) in an amount of about 50 ppm or less.

11. The method of claim 9, wherein the purified 1,1,1,3,3-pentafluoropropane (HFC-245fa) comprises 2-chloro-1,1,3,3,3-pentafluoropropane (HFC-235da) in an amount of about 50 ppm or less.

12. The method of claim 9, wherein the purified 1,1,1,3,3-pentafluoropropane (HFC-245fa) comprises 1,1,1,3,3,3-hexafluoropropane (HFC-236fa) in an amount of about 50 ppm or less.

13. The method of claim 9, wherein the purified 1,1,1,3,3-pentafluoropropane (HFC-245fa) comprises 1,1,2,3,3,3-hexafluoropropane (HFC-236ea) in an amount of 50 ppm or less.

14. The method of claim 9, wherein the purified HFO-E-1,3,3,3-tetrafluoropropene (trans-HFO-1234ze) is at least 99.999% pure and includes 3 ppm or less 1,1,3,3,3-pentafluoropropene (HFO-1225zc).

15. The method of claim 9, wherein the purified HFO-E-1,3,3,3-tetrafluoropropene (trans-HFO-1234ze) is at least 99.9995% pure and includes 3 ppm or less 1,1,3,3,3-pentafluoropropene (HFO-1225zc).

16. The method of claim 9, further comprising the additional step, prior to step (d), of passing the HFO-E-1,3,3,3-tetrafluoropropene (trans-HFO-1234ze) through at least one of a water scrubber, a caustic scrubber and a sulfuric acid drier.

17. The method of claim 9, wherein the purified HFO-E-1,3,3,3-tetrafluoropropene (trans-HFO-1234ze) is at least 99.999% pure.

* * * * *